US00PP28119P2

(12) United States Plant Patent
van den Hoogen

(10) Patent No.: US PP28,119 P2
(45) Date of Patent: Jun. 13, 2017

(54) ***HYPERICUM* PLANT NAMED 'ALLLIPST'**

(50) Latin Name: *Hypericum hybrida*
Varietal Denomination: Alllipst

(71) Applicant: Wilhelmus T. J. van den Hoogen, Cuijk (NL)

(72) Inventor: Wilhelmus T. J. van den Hoogen, Cuijk (NL)

(73) Assignee: Allplants Holding B.V., Cuijk (NL)

( * ) Notice: Subject to any disclaimer, the term of this patent is extended or adjusted under 35 U.S.C. 154(b) by 0 days.

(21) Appl. No.: 14/998,867

(22) Filed: Feb. 23, 2016

(51) Int. Cl.
*A01H 5/02* (2006.01)

(52) U.S. Cl.
USPC ..... Plt./442

(58) Field of Classification Search
USPC ..... Plt./442
CPC ..... A01H 5/02
See application file for complete search history.

*Primary Examiner* — Kent L Bell
(74) *Attorney, Agent, or Firm* — C.A. Whealy

(57) ABSTRACT

A new and distinct cultivar of *Hypericum* plant named 'Alllipst', characterized by its broadly upright plant habit; moderately vigorous growth habit; dark green-colored leaves; freely flowering habit and high fruit density; glossy reddish pink-colored fruits; and suitability as a cut flower plant.

3 Drawing Sheets

Botanical designation: *Hypericum hybrida.*
Cultivar denomination: 'ALLLIPST'.

BACKGROUND OF THE INVENTION

The present invention relates to a new and distinct cultivar of *Hypericum* plant, botanically known as *Hypericum hybrida*, typically grown as a cut flower plant and hereinafter referred to by the name 'Alllipst'.

The new *Hypericum* plant is a product of a planned breeding program conducted by the Inventor in Cuijk, The Netherlands. The objective of the breeding program is to create new cut flower *Hypericum* plants with numerous attractive glossy fruits.

The new *Hypericum* plant originated from an open-pollination in September, 2010 in Cuijk, The Netherlands of a proprietary selection of *Hypericum hybrida* identified as code number C10-289, not patented, as the female, or seed parent with an unknown selection of *Hypericum hybrida* as the male, or pollen, parent. The new *Hypericum* plant was discovered and selected by the Inventor as a single flowering plant from within the progeny of the stated open-pollination in a controlled outdoor nursery environment in Cuijk, The Netherlands in October, 2011.

Asexual reproduction of the new *Hypericum* plant by vegetative cuttings in a controlled outdoor nursery environment in Cuijk, The Netherlands since October, 2011 has shown that the unique features of this new *Hypericum* plant are stable and reproduced true to type in successive generations.

SUMMARY OF THE INVENTION

Plants of the new *Hypericum* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Alllipst'. These characteristics in combination distinguish 'Alllipst' as a new and distinct *Hypericum* plant:

1. Broadly upright plant habit.
2. Moderately vigorous growth habit.
3. Dark green-colored leaves.
4. Freely flowering habit and high fruit density.
5. Glossy reddish pink-colored fruits.
6. Suitable as a cut flower plant.

Plants of the new *Hypericum* differ primarily from plants of the female parent selection in the following characteristics:

1. Plants of the new *Hypericum* have narrower leaves than plants of the female parent selection.
2. Plants of the new *Hypericum* and the female parent selection differ in fruit color as fruits of the female parent selection are red in color.
3. Plants of the new *Hypericum* and the female parent selection differ in fruit shape as apices of fruits of the new *Hypericum* are more pointed than and not as flat as apices of fruits of the female parent selection.

Plants of the new *Hypericum* can be compared to plants of the *Hypericum hybrida* 'Alldiablo', not patented. In side-by-side comparisons conducted in Cuijk, The Netherlands, plants of the new *Hypericum* differ primarily from plants of 'Alldiablo' in the following characteristics:

1. Plants of the new *Hypericum* and 'Alldiablo' differ in fruit color as fruits of 'Alldiablo' are light pink in color.
2. Fruits of the new *Hypericum* are glossier than fruits of plants of 'Alldiablo'.

BRIEF DESCRIPTION OF THE PHOTOGRAPHS

The accompanying colored photographs illustrate the overall appearance of the new *Hypericum* plant showing the colors as true as it is reasonably possible to obtain in colored reproductions of this type. Colors in the photographs may differ slightly from the color values cited in the detailed botanical description which accurately describe the actual colors of the new *Hypericum* plant.

The photograph on the first sheet is a side perspective view of a flowering plant of 'Alllipst' grown in a container.

The photograph on the second sheet is a close-up view of the upper surface of a typical leaf of 'Alllipst'.

The photograph on the third sheet is a close-up view of typical developed fruits of 'Alllipst'.

DETAILED BOTANICAL DESCRIPTION

Plants used for the aforementioned photographs and following description were grown in September in an outdoor nursery in Cuijk, The Netherlands and under cultural practices typical of commercial cut flower *Hypericum* production. During the production of the plants, day temperatures ranged from 13° C. to 26° C. and night temperatures ranged from 6° C. to 16° C. Plants were six months old when the photographs and description were taken. In the following description, color references are made to The Royal Horticultural Society Colour Chart, 2015 Edition, except where general terms of ordinary dictionary significance are used.

Botanical classification: *Hypericum hybrida* 'Alllipst'.

Parentage:

*Female, or seed, parent*.—Proprietary selection of *Hypericum hybrida* identified as code number C10-289, not patented.

*Male, or pollen, parent*.—Unknown selection of *Hypericum hybrida*, not patented.

Propagation:

*Type cutting*.—Vegetative cuttings.

*Time to initiate roots, summer*.—About 10 to 14 days at temperatures ranging from 12° C. to 30° C.

*Time to produce a rooted young plant, summer*.—About 24 to 32 days at temperatures ranging from 12° C. to 30° C.

*Root description*.—Fine, fleshy; typically white in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Perennial shrub; broadly upright plant habit; moderately vigorous growth habit.

*Branching habit*.—Freely basal branching habit, about 23 lateral branches develop per plant.

*Plant height*.—About 53.1 cm.

*Plant width* (*spread*).—About 42.3 cm.

*Lateral branch description*.—Length: About 20.7 cm. Diameter: About 2.5 mm. Internode length: About 5.4 cm. Strength: Moderately strong to strong. Texture and luster: Glabrous; moderately glossy. Color, developing: Close to 145B to 145C. Color, fully developed: Close to N199C to N199D.

Leaf description:

*Arrangement*.—Opposite, simple; sessile.

*Length*.—About 6.8 cm.

*Width*.—About 3.8 cm.

*Shape*.—Ovate.

*Apex*.—Bluntly acute.

*Base*.—Truncate to obtuse.

*Margin*.—Entire.

*Texture and luster, upper and lower surfaces*.—Slightly rugose; glabrous; slightly glossy.

*Venation pattern*.—Pinnate.

*Color*.—Developing leaves, upper surface: Close to 146A. Developing leaves, lower surface: Close to 146B to 146C tinged with close to 152B. Fully expanded leaves, upper surface: Darker than between 139A and N189A; venation, close to 144B. Fully expanded leaves, lower surface: Close to 147B; venation, close to 144B.

Flower description:

*Flower type, arrangement and flowering habit*.—Single rotate flowers arranged in terminal and axillary compound cymes; freely flowering habit with about eight flowers per cyme and about 250 flowers developing per plant; flowers face mostly upright.

*Fragrance*.—None detected.

*Natural flowering season*.—Plants flower continuously from late June to early September in The Netherlands.

*Flower longevity*.—Flowers last about two or three days on the plant; flowers not persistent.

*Fruit longevity* (*postproduction*).—About 30 days.

*Flower buds*.—Length: About 7 mm. Diameter: About 7 mm. Shape: Roughly globular. Color: Close to 13A.

*Inflorescence height*.—About 5.6 cm.

*Inflorescence diameter*.—About 6.8 cm.

*Flower diameter*.—About 2.7 cm.

*Flower depth* (*height*).—About 1.7 cm.

*Petals*.—Quantity and arrangement: Five in a single whorl. Length: About 1.2 cm. Width: About 7 mm. Shape: Ovate, concave; horizontal to slightly reflexed. Apex: Acute, unequal. Base: Attenuate. Margin: Entire. Texture and luster, upper surface: Smooth, glabrous; matte. Texture and luster, lower surface: Smooth, glabrous; slightly glossy. Color: When opening, upper and lower surfaces: Close to 13B. Fully opened, upper and lower surfaces: Close to 13A; color becoming closer to 15B with development.

*Sepals*.—Quantity and arrangement: Five in a single whorl. Length: About 9 mm. Width: About 6 mm. Shape: Ovate; moderately reflexed. Apex: Acute. Base: Broadly cuneate. Margin: Entire. Texture and luster, upper and lower surfaces: Smooth, glabrous; dull. Color: When opening, upper surface: Close to 141A; margins, close to 185A. When opening, lower surface: Close to 137C; margins, close to 185A. Fully opened, upper surface: Close to 141B; margins, close to 178A. Fully opened, lower surface: Close to 141C; margins, close to 178A.

*Peduncles*.—Length: About 1.9 cm. Diameter: About 2 mm. Texture: Smooth, glabrous. Strength: Moderately strong. Aspect: Main peduncles, erect; lateral peduncles, about 40° from main peduncles axis. Color: Close to 146D.

*Pedicels*.—Length: About 1.3 cm. Diameter: About 1.5 mm. Texture: Smooth, glabrous. Strength: Moderately strong. Aspect: Main pedicels, erect; lateral pedicels, about 45° from main peduncles axis. Color: Close to 144A.

*Reproductive organs*.—Stamens: Quantity per flower: About 90. Filament length: About 1 mm. Filament color: Close to 13A to 13B. Anther length: About 0.5 mm. Anther shape: Broadly oval; dorsifixed. Anther color: Close to 19A. Pollen amount: Scarce. Pollen color: Close to 11A. Pistils: Quantity per flower: Single pistil with three stigmas. Pistil length: About 4 mm. Stigma shape: Club-shaped. Stigma color: Close to 31C. Style length: About 3.5 mm. Style color: Close to 151D. Ovary color: Close to 150D.

*Fruits*.—Quantity per plant: About 250. Length: About 1.5 cm. Diameter: About 1.2 cm. Shape: Roughly globular. Texture and luster: Smooth, glabrous; glossy. Color: Close to N45B.

*Seeds*.—Quantity per fruit: More than 100. Length: About 0.9 mm. Diameter: About 0.5 mm. Color: Close to 200A.

Disease & pest resistance: Plants of the new *Hypericum* have not been observed to be resistant to pathogens and pests common to *Hypericum* plants.

Temperature tolerance: Plants of the new *Hypericum* have been observed to tolerate high temperatures about 30° C. and to be hardy to USDA Hardiness Zone 7.

It is claimed:

1. A new and distinct *Hypericum* plant named 'Alllipst' as illustrated and described.

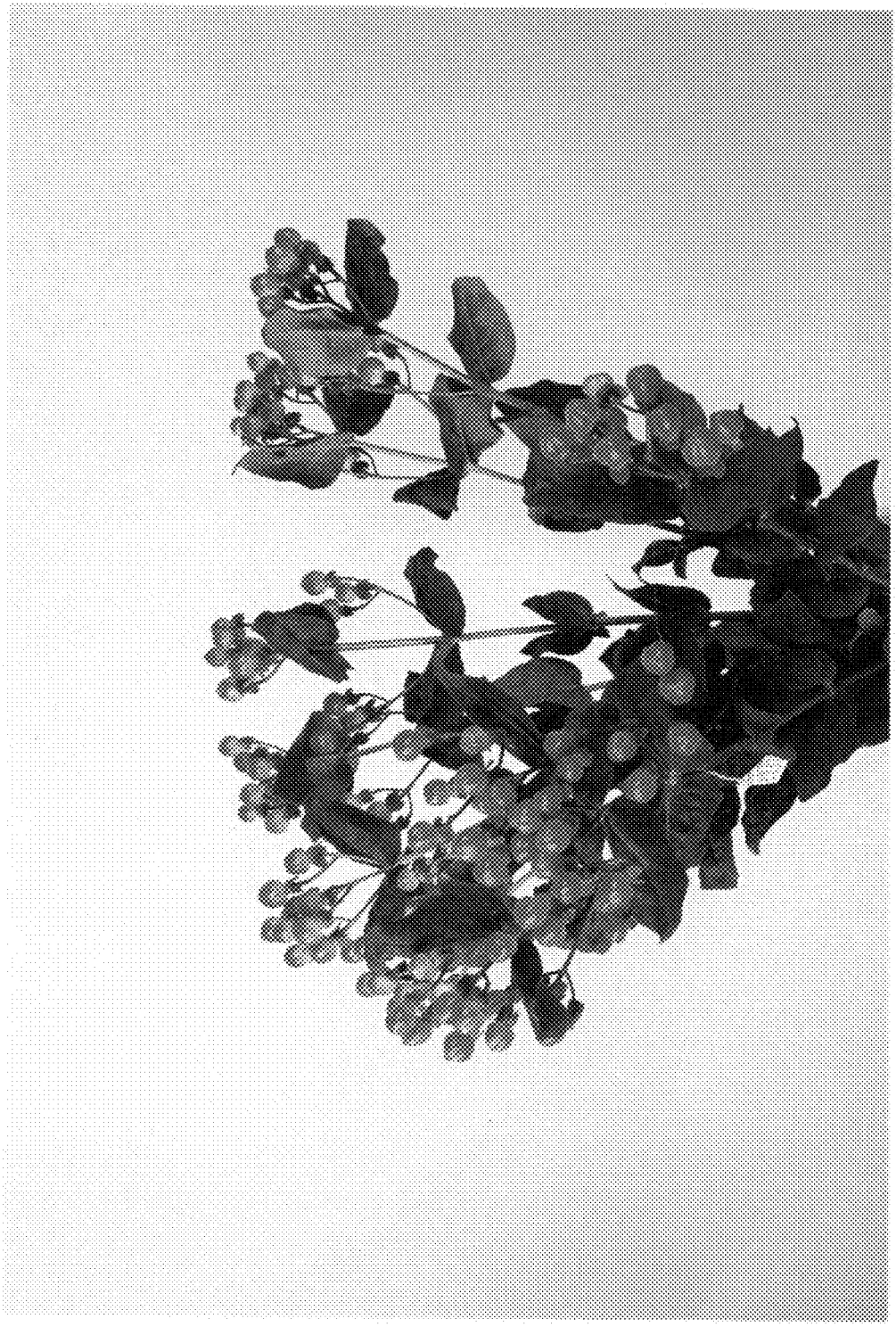

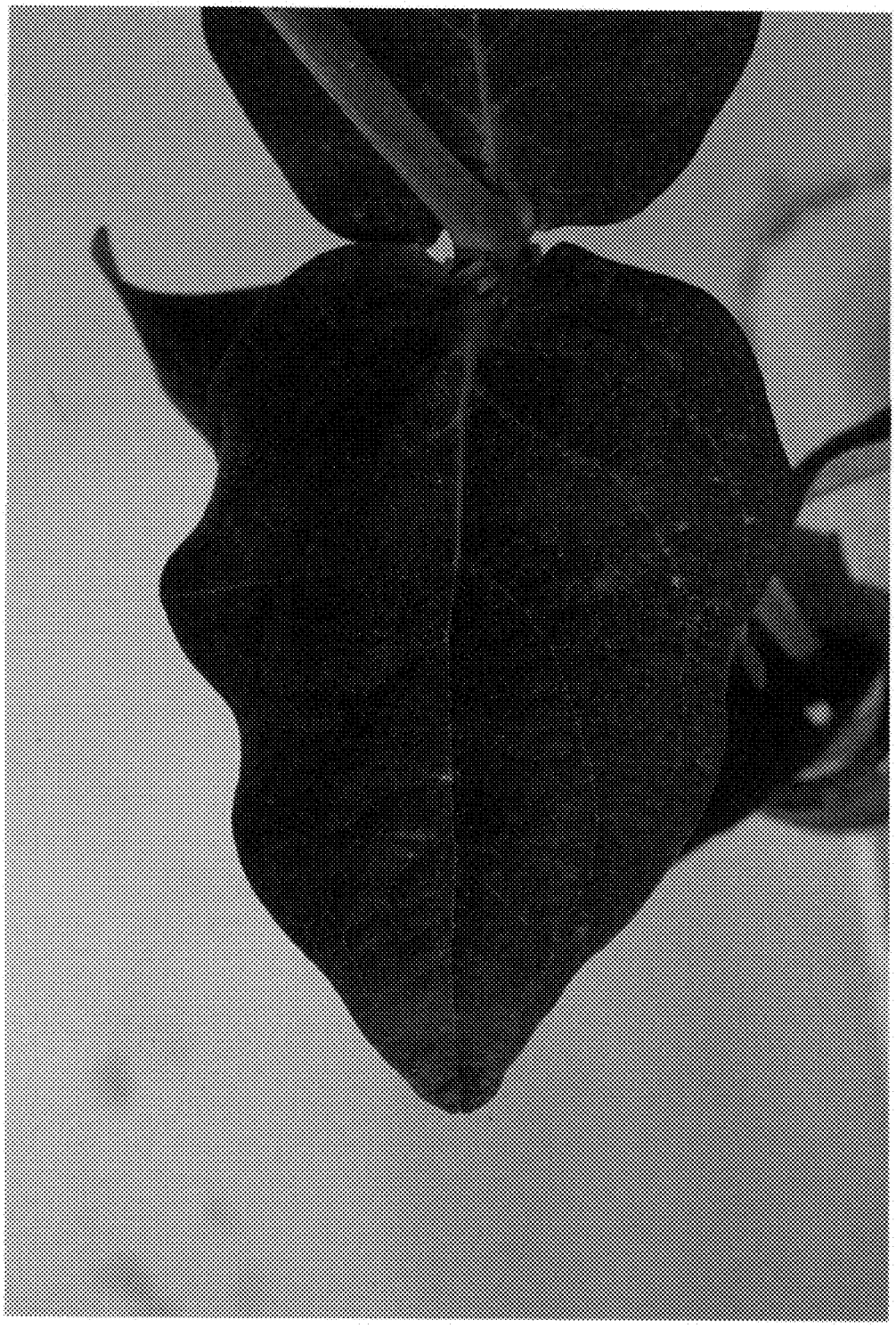

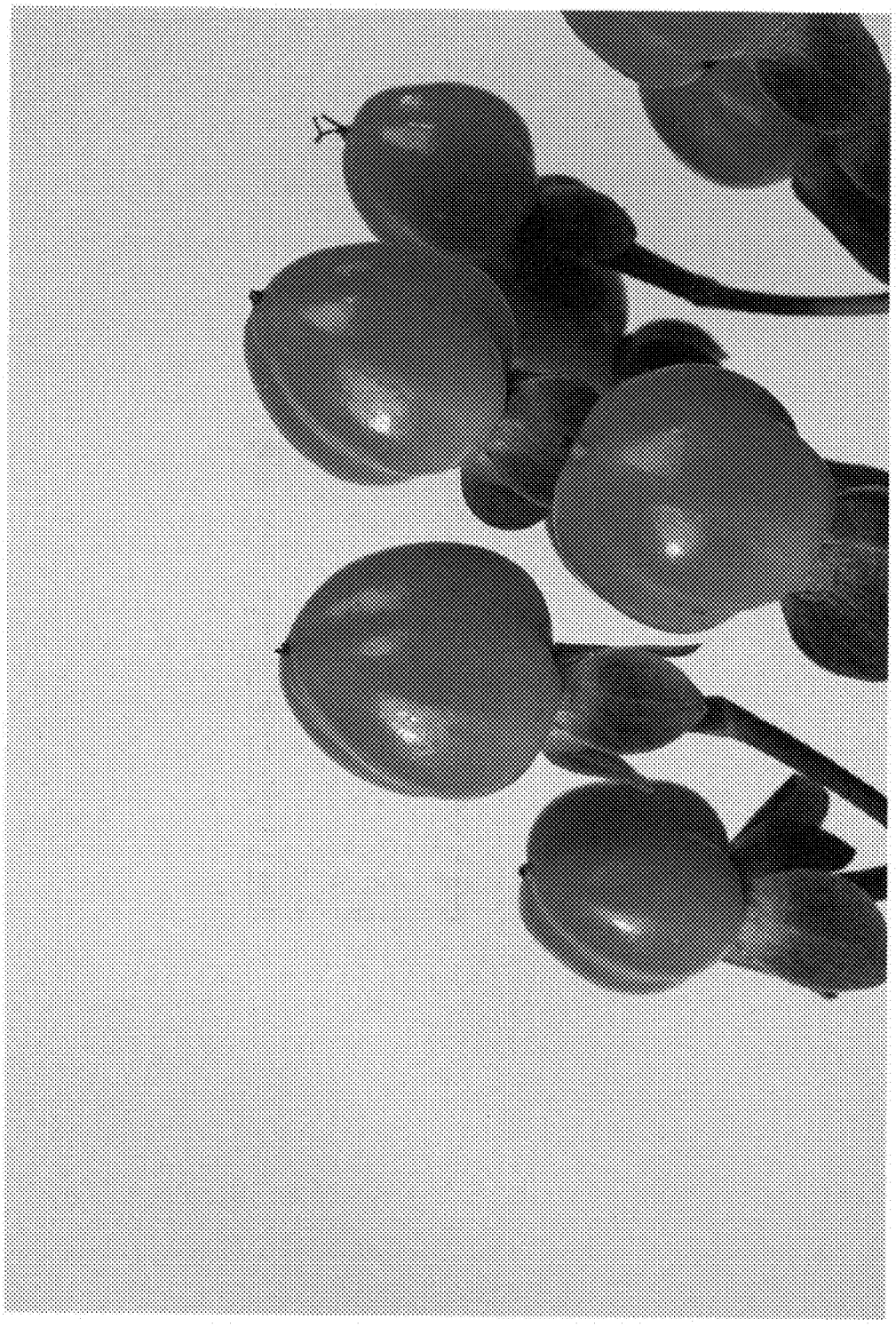

* * * * *